United States Patent
Taubman et al.

(10) Patent No.: US 9,001,854 B2
(45) Date of Patent: Apr. 7, 2015

(54) METHODS FOR DETERMINING OPTICAL POWER, FOR POWER-NORMALIZING LASER MEASUREMENTS, AND FOR STABILIZING POWER OF LASERS VIA COMPLIANCE VOLTAGE SENSING

(75) Inventors: Matthew S. Taubman, West Richland, WA (US); Mark C. Phillips, Kennewick, WA (US)

(73) Assignee: Battelle Memorial Institute, Richland, WA (US)

( * ) Notice: Subject to any disclaimer, the term of this patent is extended or adjusted under 35 U.S.C. 154(b) by 231 days.

(21) Appl. No.: 13/566,790

(22) Filed: Aug. 3, 2012

(65) Prior Publication Data

US 2013/0195130 A1    Aug. 1, 2013

Related U.S. Application Data

(60) Provisional application No. 61/592,297, filed on Jan. 30, 2012, provisional application No. 61/593,991, filed on Feb. 2, 2012.

(51) Int. Cl.
*H01S 3/13* (2006.01)
*H01S 5/068* (2006.01)
(Continued)

(52) U.S. Cl.
CPC .......... *H01S 5/06808* (2013.01); *G01N 21/031* (2013.01); *G01N 21/39* (2013.01); *H01S 5/0028* (2013.01); *H01S 5/0617* (2013.01); *H01S 5/0687* (2013.01); *H01S 5/141* (2013.01); *H01S 5/143* (2013.01); *H01S 5/3401* (2013.01); *G01N 2021/399* (2013.01); *G01N 2021/7776* (2013.01); *G01N 2201/0612* (2013.01); *H01S 5/3402* (2013.01); *B82Y 20/00* (2013.01)

(58) Field of Classification Search
CPC .......... H01S 5/068; H01S 5/14; H01S 5/3401
USPC ......................................... 372/29.02, 29.021
See application file for complete search history.

(56) References Cited

U.S. PATENT DOCUMENTS

| 4,872,173 A | 10/1989 | Richardson |
| 2004/0202210 A1 | 10/2004 | Thornton |

(Continued)

OTHER PUBLICATIONS

International Search Report/Written Opinion for International Application No. PCT/US2012/065593, International Filing Date Nov. 16, 2012, Date of Mailing Mar. 6, 2013.

*Primary Examiner* — Armando Rodriguez
(74) *Attorney, Agent, or Firm* — James D. Matheson

(57) ABSTRACT

A method is disclosed for power normalization of spectroscopic signatures obtained from laser based chemical sensors that employs the compliance voltage across a quantum cascade laser device within an external cavity laser. The method obviates the need for a dedicated optical detector used specifically for power normalization purposes. A method is also disclosed that employs the compliance voltage developed across the laser device within an external cavity semiconductor laser to power-stabilize the laser mode of the semiconductor laser by adjusting drive current to the laser such that the output optical power from the external cavity semiconductor laser remains constant.

12 Claims, 6 Drawing Sheets

(51) Int. Cl.
  *G01N 21/39* (2006.01)
  *H01S 5/00* (2006.01)
  *B82Y 20/00* (2011.01)
  *G01N 21/03* (2006.01)
  *H01S 5/06* (2006.01)
  *H01S 5/0687* (2006.01)
  *H01S 5/14* (2006.01)
  *H01S 5/34* (2006.01)
  *G01N 21/77* (2006.01)

(56) References Cited

U.S. PATENT DOCUMENTS

2006/0193354 A1* 8/2006 Rosenblatt ............... 372/29.023
2008/0130695 A1* 6/2008 Riddle et al. ..................... 372/33
2012/0183004 A1* 7/2012 Kupershmidt ........... 372/29.011

* cited by examiner

METHODS FOR DETERMINING OPTICAL POWER, FOR POWER-NORMALIZING LASER MEASUREMENTS, AND FOR STABILIZING POWER OF LASERS VIA COMPLIANCE VOLTAGE SENSING

CROSS REFERENCE TO RELATED APPLICATIONS

This application claims priority from U.S. Provisional Patent Application No.: 61/592,297 filed 30 Jan. 2012 entitled "Gas Detection via Compliance Voltage Measurement in an External Cavity Semiconductor Laser", and U.S. Provisional Patent Application No.: 61/593,991 filed 31 May 2012 entitled "Methods for Normalizing Power of Spectroscopic Signatures from Chemical Sensors Employing Lasers and for Stabilizing Power of Lasers via Compliance Voltage Sensing", which references are incorporated herein in their entirety.

STATEMENT REGARDING RIGHTS TO INVENTION MADE UNDER FEDERALLY-SPONSORED RESEARCH AND DEVELOPMENT

This invention was made with Government support under Contract DE-AC05-76RLO1830 awarded by the U.S. Department of Energy. The Government has certain rights in the invention.

FIELD OF THE INVENTION

The invention relates to laser-based chemical detection and sensors. More particularly, the invention relates to chemical detection using an external cavity laser and power stabilization of an external cavity laser.

BACKGROUND OF THE INVENTION

Laser-based sensors that interrogate chemical samples across a range of optical wavelengths often make use of a tunable laser system such as a tunable external cavity laser (ECL). As the laser scans across its wavelength range, the output power of the ECL varies. The output power typically reaches a maximum somewhere in the middle of the scan, and falls to zero on either edge of the scan. In order to compensate for various aspects of the power variation, a separate photo-detector can be employed to measure the power output of the laser independent of any absorption signatures. The separate photo detector may be separate from any photo detector involved in the detection process. Absorption spectra derived from the sensor can then be divided by the power spectrum to provide a power-normalized spectrum. Need for an extra photodetector is a limitation of chemical sensors employing power normalization because of the increased size, weight, and power required. The present invention addresses these and other problems by providing laser configurations and methods that obviate the need for an extra photo detector dedicated specifically to measure power output of the laser (i.e., for power normalization) for chemical sensing applications, thus reducing the size, weight, and power required for such systems. It further provides a method for determining the circulating power of external cavity lasers and for precise and sensitive detection of analytes without the need for a separate detector.

SUMMARY OF THE PRESENT INVENTION

A method is described for determining a circulating optical power of an external cavity laser (ECL). The method may include: driving a laser device within the ECL with a current through the laser device, measuring the compliance voltage across the laser device within the ECL, and applying a mathematical function to the compliance voltage to determine the circulating optical power within the ECL. The method may also include sweeping a wavelength of the ECL with a sweep signal while measuring the compliance voltage to generate a compliance voltage spectrum as a function of the wavelength. A spectrum of compliance voltages may also be obtained as the wavelength of the ECL is scanned in accordance with the sweep signal. A mathematical function may be applied to the compliance voltage spectrum to obtain a circulating optical power spectrum. The mathematical function applied to the compliance voltage may be any valid mathematical function including multiplication functions, division functions, linear functions, polynomial functions, square root functions, raising to mathematical power functions, exponential functions, logarithmic functions, trigonometric functions, binomial functions, and combinations of these.

The mathematical function may be a single-valued function that acts solely on or includes the compliance voltage as an input and produces an optical power as an output. The mathematical function may also be a binary function that acts on or includes two inputs, e.g., the compliance voltage and the laser drive current, or the ECL sweep signal, and produces an optical power as an output. The mathematical function may also be a ternary function that acts on three inputs, e.g., the compliance voltage, the laser drive current, and the sweep signal to produce an optical power as an output.

The optical output power of the ECL may also be derived by further multiplying the circulating optical power by a constant value. When the ECL is swept, the optical output power spectrum of the ECL may be derived by further multiplying the circulating optical power spectrum by a mathematical function of the sweep signal.

A method is also disclosed for obtaining a power-normalized laser measurement with an ECL. The method may include: driving a laser device located within the ECL with a current through the laser device, obtaining a laser measurement with the ECL, measuring a compliance voltage of the laser device, and combining the laser measurement with the compliance voltage or some function thereof to obtain a power-normalized laser measurement. The laser measurement may be a single measurement from a sensor incorporating an ECL, or a spectrum of measurements.

The laser measurement may also be a chemical detection measurement. The laser measurement may be a distance measurement. The laser measurement may be a density measurement. The laser measurement may also be a temperature measurement.

The compliance voltage measurement may be made simultaneously with the laser measurement or independently. The compliance voltage measurement may include a spectrum of compliance voltage values obtained as a function of wavelength as the ECL is scanned in wavelength. The laser measurement may also be combined with a mathematical function of the compliance voltage. The compliance voltage measurement or spectrum may be used to determine an optical power or spectrum. The laser measurement or spectrum may also be divided by the optical power or spectrum to produce a power-normalized laser measurement. The laser measurement or spectrum may also be divided by the compliance voltage spectrum or a function thereof to produce a normalized absorption spectrum.

Lasers can include, but are not limited to, e.g., semiconductor lasers, diode lasers, quantum cascade (QC) lasers, inter-band cascade lasers (iCLs), continuous wave (CW)

lasers, pulsed lasers, distributed feedback (DFB) quantum cascade (QC) lasers (DFB-QCLs), components thereof, and combinations of these various lasers and laser systems. The ECL may be an external cavity diode laser (ECDL). The ECL may also be an external cavity quantum cascade laser (EC-QCL). The ECL may also be an external cavity interband cascade laser (ECICL).

Analytes can include gases, liquids, aerosols, solids, plasmas, and combinations of these various analyte forms. The chemical detection method may include a direct photo-detection of light after passing through an analyte. The analyte may be contained within or passed through a sample cell. Or, the analyte may be contained within, or passed through, a multi-pass optical cell such as a White cell or a Herriott cell. The analyte may also be external to, and at a remote distance from, the chemical sensor.

The chemical detection method may include photo-acoustic detection. And, the photo-acoustic detection may be performed with a photo-acoustic sensor that includes an acoustic cell and a microphone. The photo-acoustic sensor may also include a tuning fork.

The chemical detection method may also include photo-thermal detection. For example, the photo-thermal detection may occur within a closed cell. Or, the photo-thermal detection may occur external to, and/or at a remote distance from, the chemical sensor.

The output from the ECL may be modulated in frequency, and the laser measurement may include a demodulated detection process. The output from the ECL may be modulated in amplitude, and the laser measurement may include a demodulated detection process.

A method is also disclosed for stabilizing the power of an external cavity laser (ECL). The method may include: obtaining the compliance voltage or some function thereof of a laser device within an ECL, passing the compliance voltage signal to a feedback amplifier, passing the output of the feedback amplifier to a current controller supplying current to the laser device to control the optical power circulating within the ECL and the compliance voltage across the laser device, and adjusting gains and filter functions within the feedback amplifier while scanning the optical wavelength of the ECL to stabilize power of the output from the ECL. The feedback amplifier may include amplifiers, filters, notches, offsets, summing and difference modules, and combinations of these components, but is not limited to these components.

A method is also disclosed for stabilizing an optical power of an external cavity laser (ECL). The method may include: driving a laser device located within the external cavity laser with a current through the laser device from a current controller, measuring the compliance voltage across the laser device, applying a mathematical function to the compliance voltage to produce an optical power signal proportional to an optical power of the external cavity laser, feeding the optical power signal back to the current controller to change the current delivered to the laser device, and adjusting feedback parameters to stabilize the optical power of the external cavity laser. Feedback parameters can include, but are not limited to, e.g., phase, amplitude and bandwidth of the optical power signal. The optical power may be a circulating optical power. The optical power may also be an output optical power.

Various advantages and novel features of the present invention are described herein and will become further readily apparent to those skilled in this art from the following detailed description. In the preceding and following descriptions, the various embodiments, including the preferred embodiments, have been shown and described. Included herein is a description of the best mode contemplated for carrying out the invention. As will be realized, the invention is capable of modification in various respects without departing from the invention. Accordingly, the drawings and description of the preferred embodiments set forth hereafter are to be regarded as illustrative in nature, and not as restrictive.

DETAILED DESCRIPTION

System configurations and processes are detailed that employ an external cavity laser (ECL) as a light source for chemical detection (i.e., as a chemical sensor). Compliance voltage signal across the laser device (LD) located within the ECL may be used (i.e., in chemical sensors using this type of laser) to develop or derive a signal proportional to the power output of the ECL. The proportional signal may then be used to normalize spectra obtained from various embodiments detailed herein and to stabilize power output of ECLs. The present invention uses compliance voltage monitoring techniques to obtain information regarding optical power that obviates need for photodetectors dedicated specifically for power normalization, which can reduce the size, weight, and power required for such systems. The following description details a best mode of at least one embodiment of the present invention. While various embodiments describe use of an external cavity laser (ECL), the invention is not intended to be limited thereto. For example, it will be clear from the description that the invention is susceptible of various modifications and alternative constructions. Thus, it should be understood that there is no intention to limit the invention to the specific form disclosed, but, on the contrary, the invention is to cover all modifications, alternative constructions, and equivalents falling within the spirit and scope of the invention as defined in the claims. Therefore the present description should be seen as illustrative and not limiting.

Figure 1:
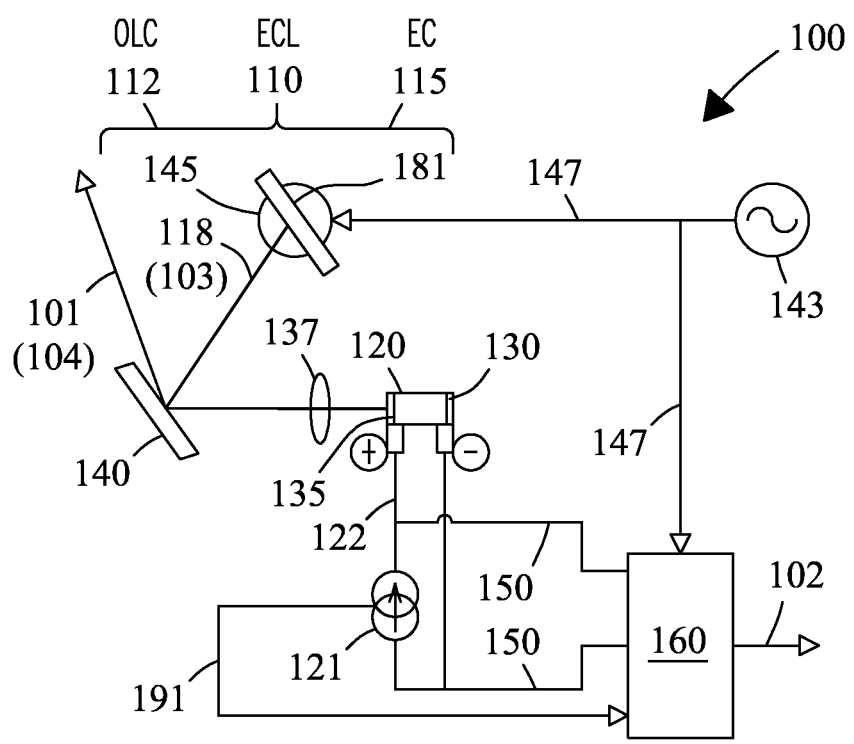
FIG. 1 shows an external cavity laser with power measurement that employs compliance voltage measurement to obtain circulating optical power and output optical power.

FIG. 1 shows an external cavity laser (ECL) with power measurement (ECLPM) 100 arranged in a Littman-Metcalf configuration that employs compliance voltage measurement to obtain circulating optical power and/or output optical power. ECLPM 100 may also be used as a power-stabilized light source, as described further herein. In some embodiments, ECLPM 100 may include an ECL 110 including a laser device (LD) 120 with a high-reflectance mirror coating 130 and anti-reflection coating 135, focusing lens 137, a wavelength-selective element or device 140 such as an optical grating 140, and an external mirror 181. Optical laser cavity (OLC) 112 in which an ECL optical mode 118 (or laser mode) exists may be defined by the following items: LD 120, optical grating 140 and external mirror 181. ECL optical mode 118 includes a circulating optical power 103. ECLPM 100 may generate an output beam 101 that is distinct from ECL mode 118. Output beam 101 includes an optical output power 104. ECL mode 118 may be common to both LD 120 and EC 115. External cavity (EC) 115 may be that part of laser cavity 112 external to LD 120. External mirror 181 may be further mounted on an actuator 145 that tunes a wavelength of ECL 110. ECLPM 100 may further include a current controller 121 which supplies LD 120 with current 122, and produces current monitor (signal) 191. Compliance voltage 150 appearing across LD 120 (and thus simultaneously across current controller 121) may be passed to a measurement system 160 to produce an output value 102 proportional to the circulating optical power 103. In some embodiments, output value 102 may also be proportional to the optical output power 104.

Measurement system 160 may include: amplifiers, servos, filters, and computers or CPUs, but is not limited thereto. Measurement system 160 may apply a mathematical function to the compliance voltage 150 which may consist of one or more of square root functions, raising to a mathematical power function, linear functions, polynomial functions, exponential functions, logarithmic functions, trigonometric functions or binomial functions. The mathematical function within measurement system 160 may be a single-valued function that includes, e.g., only compliance voltage 150. The mathematical function within measurement system 160 may also be a binary function that includes, e.g., compliance voltage 150, and either the drive current value from drive current monitor 191, or the sweep signal 147. The mathematical function within measurement system 160 may also be a ternary function that includes, e.g., the compliance voltage 150, the drive current value from current monitor 191, and the sweep signal 147. In this way, ECLPM 100 includes a power measurement such as the circulating optical power or the output power.

Figure 2:
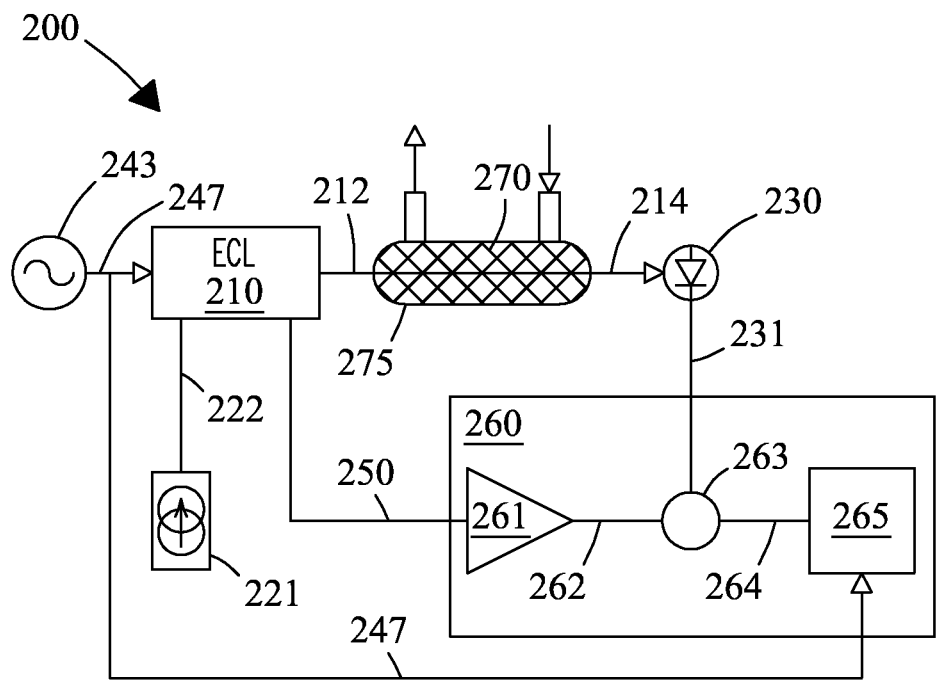
FIG. 2 shows one embodiment of an external cavity laser voltage-mediated intra-cavity power-normalized chemical sensor (EVIP-CS).

FIG. 2 shows an external cavity laser (ECL) voltage-mediated intra-cavity power-normalized (EVIP) chemical sensor (EVIP-CS) 200. An external cavity laser (ECL) 210 may be used as an optical source 210. The compliance voltage signal 250 derived from ECL 210 may be used to normalize the output 231 of chemical sensor 200 with respect to optical power. Optical output 212 of ECL 210 may be passed through gas cell 275 where it interacts with an analyte 270 or analytes 270. Remaining light 214 transmitted from gas cell 275 may be directed to a photo-detector 230. Output 231 from photo-detector 230 may be monitored by a measurement system 260. Measurement system 260 may include a combination of, e.g., passive electronic components, amplifiers, mixers, and computers or CPUs, but is not limited thereto. EVIP-CS 200 may also include a signal-generating device 243 that produces a signal 247 that scans optical output 212 of ECL 210 (e.g., in wavelength), which allows spectroscopic features of an analyte 270 or analytes 270 to be measured and evaluated. EVIP-CS 200 may also include a current controller 221 that supplies ECL 210 with current 222. Compliance voltage 250 developed within ECL 210 may be monitored by measurement system 260. Compliance voltage 250 may further be recorded simultaneously with scanning signal 247 and photo-detector output 231. Compliance voltage 250 may be acted upon by a compensating function 261 located within measurement system 260. Compensating functions include mathematical functions such as raising to a power functions, square root functions, addition functions, multiplication functions, division functions (e.g., dividing by a constant), binary functions, logarithmic functions, exponential functions, including combinations of these various functions and mathematical operations. Functions may also include amplification and gain functions, attenuation functions, filtering functions, and other related functions. No limitations are intended. For example, all functions and related operations as will be implemented by those of ordinary skill in the art in view of this disclosure are within the scope of the present invention. Compensated compliance voltage signal 262 may then be combined with photo-detector output 231 via a binary function 263 such as, e.g., division or multiplication. Output 264 of binary function 263 may be displayed with respect to, or processed as a function of, scanning signal 247 using a display system 265, processing system 265, or algorithm 265. In this manner, output 264 of EVIP-CS 200 obtained in the detection of analyte 270 may be normalized with respect to optical power (or some derivative thereof) of ECL 210.

Figure 3:
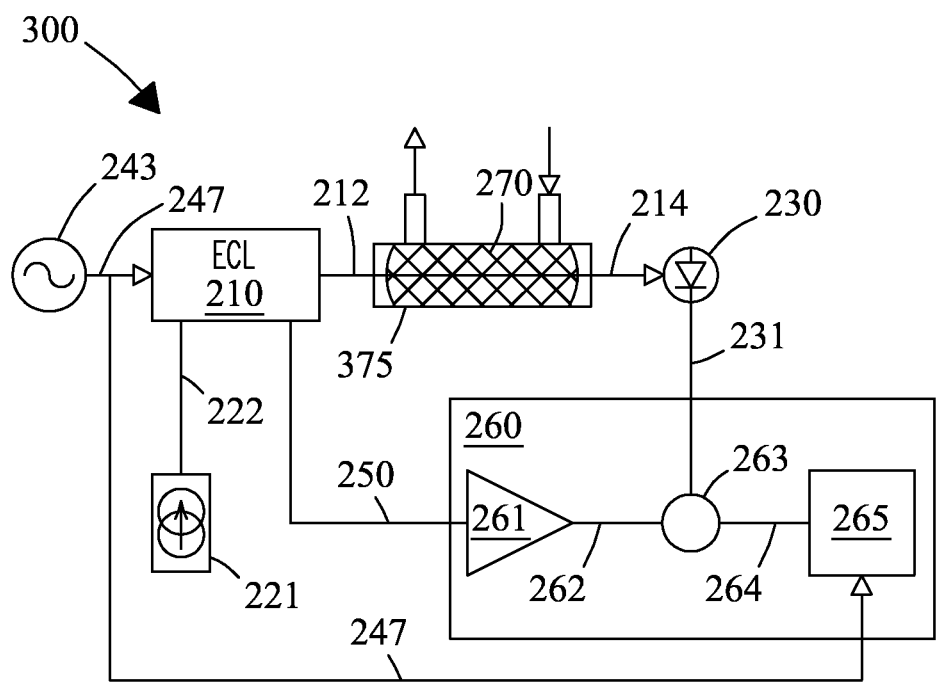
FIG. 3 shows another embodiment of an EVIP-CS.

FIG. 3 shows another embodiment of an external cavity laser (ECL) voltage-mediated intracavity power-normalized (EVIP) chemical sensor (EVIP-CS) 300. In this embodiment, gas cell (described previously in reference to FIG. 2) may be exchanged with a multipass cell 375 such as a Herriot cell or a White cell. Other components may be included as previously described for FIG. 2.

Figure 4:
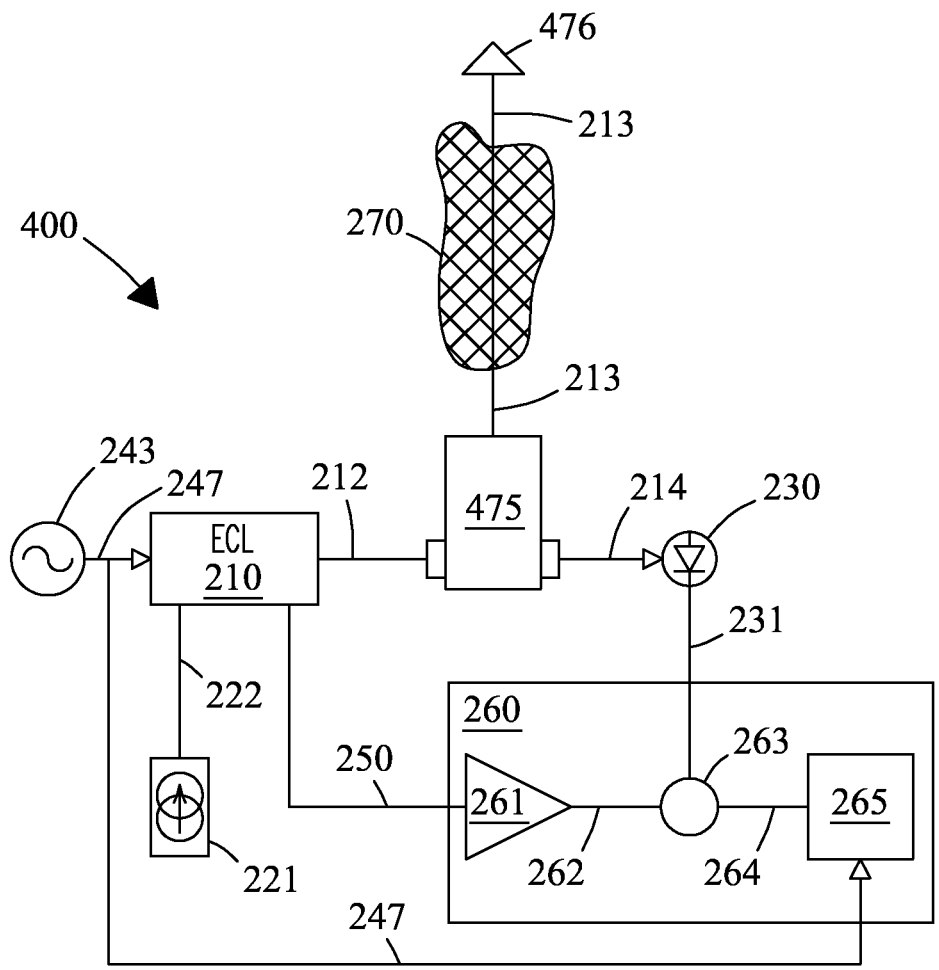
FIG. 4 shows yet another embodiment of an EVIP-CS.

FIG. 4 shows another embodiment of an external cavity laser (ECL) voltage-mediated intra-cavity power-normalized (EVIP) chemical sensor (EVIP-CS) 400. An ECL 210 may be used as an optical source 210. Compliance voltage signal 250 derived from ECL (optical source) 210 may be used to normalize output 231 of chemical sensor 300 with respect to optical power. Optical output 212 of ECL 210 may be passed into a launch-and-receive unit 475 such as an optical telescope that includes appropriate expansion and focusing optics, as well as a mechanism for differentiating light 213 launched and received from launch-and-receive unit 475. For example, light 213 may be launched some arbitrary distance from launch-and-receive unit 375 to reflector 476 and returned to launch-and-receive unit 475. Light 213 interacts with analyte 270 during its transit from launch-and-receive unit 475 to reflector 476, and during its return from reflector 476 to launch-and-receive unit 475. Light 213 received by launch-and-receive unit 475 may be transmitted to photo-detector 230 as optical beam 214. Output 231 from photo-detector 230 may in turn be monitored by measurement system 260. Other components may be included as previously described for FIG. 2.

Figure 5:
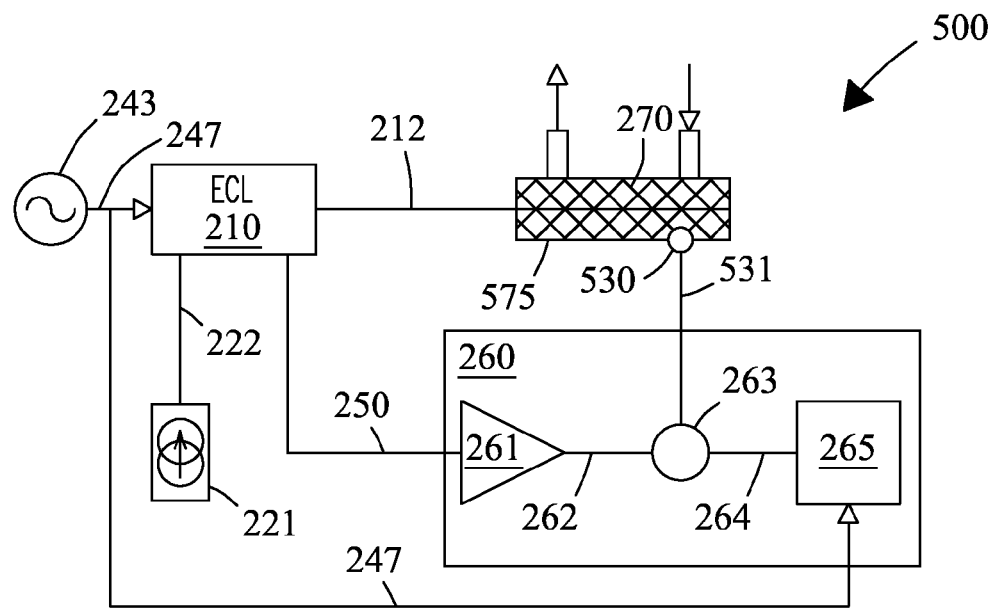
FIG. 5 shows another embodiment of an EVIP-CS of a photo-acoustic type.

FIG. 5 shows another embodiment of an external cavity laser (ECL) voltage-mediated intracavity power-normalized (EVIP) chemical sensor (EVIP-CS) 500 of a photo-acoustic type. An ECL 210 may be used as an optical source 210. Compliance voltage signal 250 derived from ECL (optical source) 210 may be used to normalize output 531 of chemical sensor 500 with respect to optical power. Optical output 212 of ECL 210 may be passed through a photo-acoustic cell 575, where output 212 interacts with analyte 270 producing an acoustic pressure wave (not shown) that may be detected by photo-acoustic sensor 530, which in turn produces output 531. Output 531 of photo-acoustic sensor 530 may be monitored by measurement system 260. Other components may be included as previously described for FIG. 2.

Figure 6:
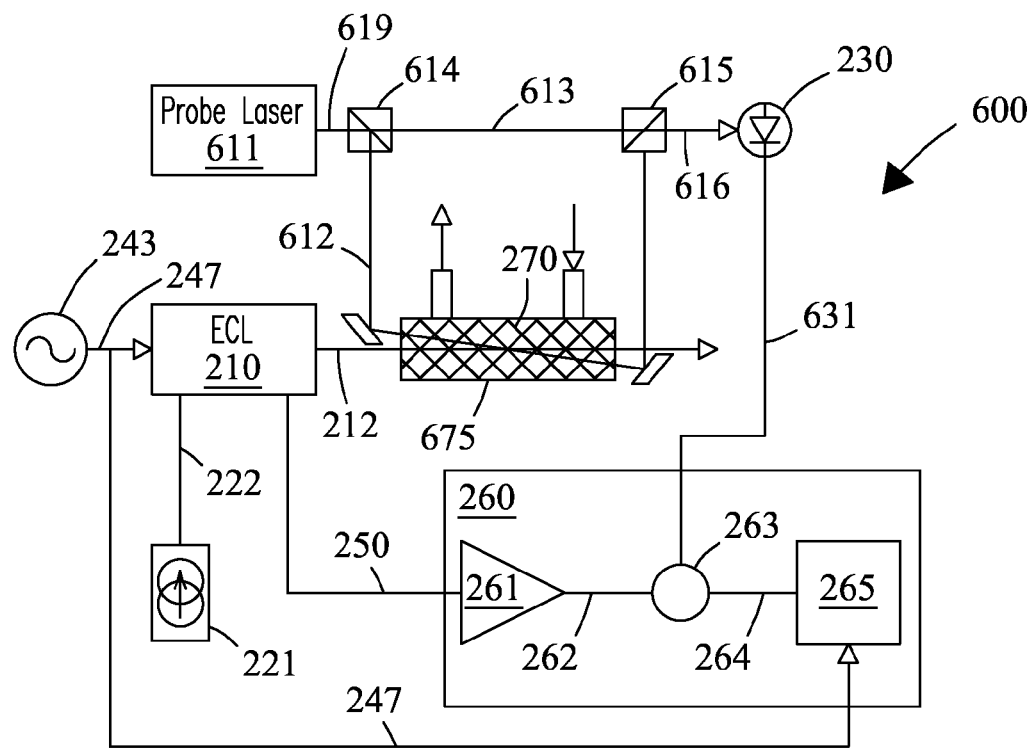
FIG. 6 shows another embodiment of an EVIP-CS of a photo-thermal type.

FIG. 6 shows another embodiment of an external cavity laser (ECL) voltage-mediated intracavity power-normalized (EVIP) chemical sensor (EVIP-CS) 600 of a photo-thermal type. An ECL 210 may be used as a first optical source 210 (i.e., a pump laser). Compliance voltage signal 250 derived from ECL (optical source) 210 may be used to normalize output 631 of chemical sensor 600 with respect to optical power. Optical output 212 from first optical source 210 of ECL 210 may be passed through a photo-thermal cell 675, where optical output 212 interacts with an analyte 270 or multiple analytes 270. Output 619 from a second optical source 611 (i.e., a probe laser 611) that may be weaker in intensity and/or of a different optical wavelength than output 212 from first optical source 210 may be split into two separate beams 612 and 613 using beamsplitter 614. Beam 612 can be passed through photo-thermal cell 675 to intercept beam 212 received from ECL 210. Upon transmission, beam 612 from photo-thermal cell 675 may be recombined with beam 613 using beam combiner 615 to produce beam 616 which may be incident upon photo-detector 230. EVIP-CS 600 may also include a signal-generating device 243 that produces a signal 247 that scans optical output 212 of ECL 210 (e.g., in wavelength), allowing analytes 270 to absorb optical energy and become thermally excited when a wavelength of optical output 212 equals that of the spectroscopic features of analyte 270. Thermal excitation of analytes 270 may cause refractive index changes that can be interferometrically detected by detector 230 due to interference changes between beams 612 and 613. EVIP-CS 600 may also include a current controller 221 that supplies ECL 210 with current 222. Compliance voltage 250 may be recorded simultaneously with scanning signal 247 and photo-detector 230 output 631. Compliance voltage 250 may be acted upon as described previously in concert with a compensating function 261 located within measurement system 260. Compensated compliance voltage signal 262 may be combined with photo-detector 230 output 631 via a binary function 263 such as, e.g., division or multiplication. Output 264 of binary function 263 may be displayed with respect to, or processed as a function of, scanning signal 247 using a display, algorithm, or processing system 265. In this manner, output 631 of EVIP-CS 600 obtained during detection of analyte 270 may be normalized with respect to optical power of ECL 210 or some derivative thereof.

Figure 7:
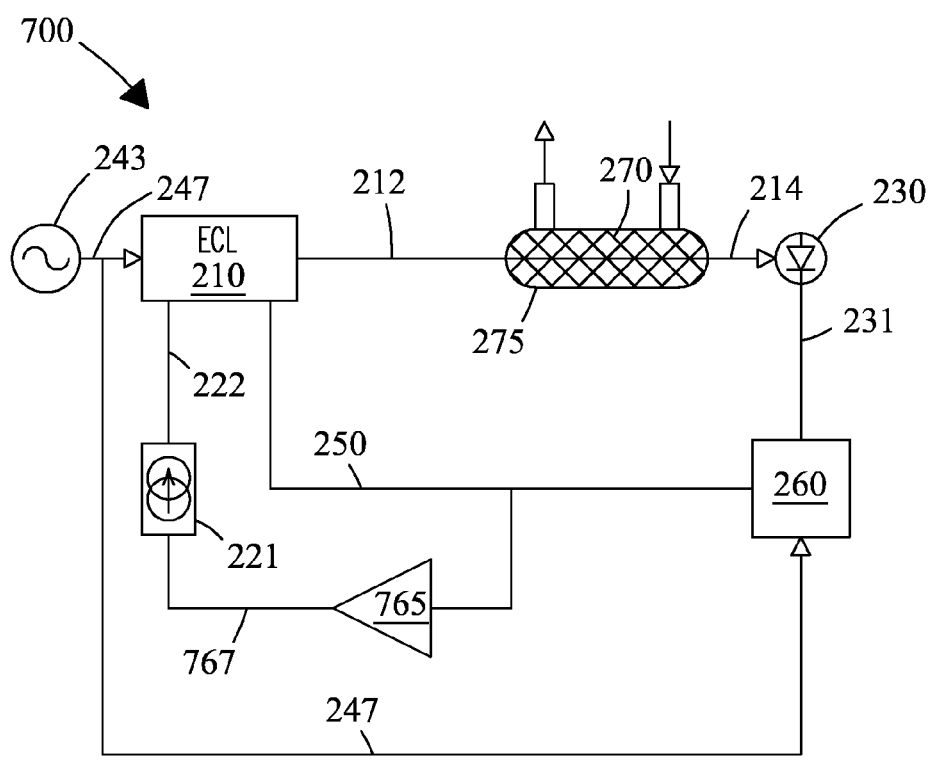
FIG. 7 shows still yet another embodiment of an EVIS-CS.

FIG. 7 shows another embodiment of an external cavity laser voltage-mediated intra-cavity power-stabilized (EVIS) chemical sensor (EVIS-CS) 700. An ECL 210 may be used as an optical source 210. Compliance voltage signal 250 derived from ECL 210 may be used to stabilize the power of output 212 of ECL 210. Optical output 212 of ECL 210 may be passed through a gas cell 275 where output 212 interacts with an analyte 270 or multiple analytes 270 in gas cell 275. Remaining light 214 transmitted from gas cell 275 may be directed to photo-detector 230. EVIS-CS 700 may also include a signal-generating device 243 that produces a signal 247 that scans optical output 212 of ECL 210 (e.g., in wavelength), which allows spectroscopic features of an analyte 270 or analytes 270 to be measured and evaluated. EVIP-CS 700 may also include a current controller 221 that supplies ECL 210 with current 222. Compliance voltage 250 developed within ECL 210 may be monitored by measurement system 260. Compliance voltage 250 may also be passed through feedback amplifier 765. Feedback amplifier 765 may include various components including, but not limited to, e.g., amplifiers, filters, notches, offsets, summing and difference modules, including combinations of these various components. No limitations are intended. Output 767 of feedback amplifier 765 may be fed to current controller 221 and used to control current 222 to keep power of output 212 of ECL 210 constant. In this manner, an optical power of output 212 from ECL 210 used within EVIS-CS 700 to detect analytes 270 may be power-stabilized using compliance voltage 250 and feedback amplifier 765.

Figure 8:
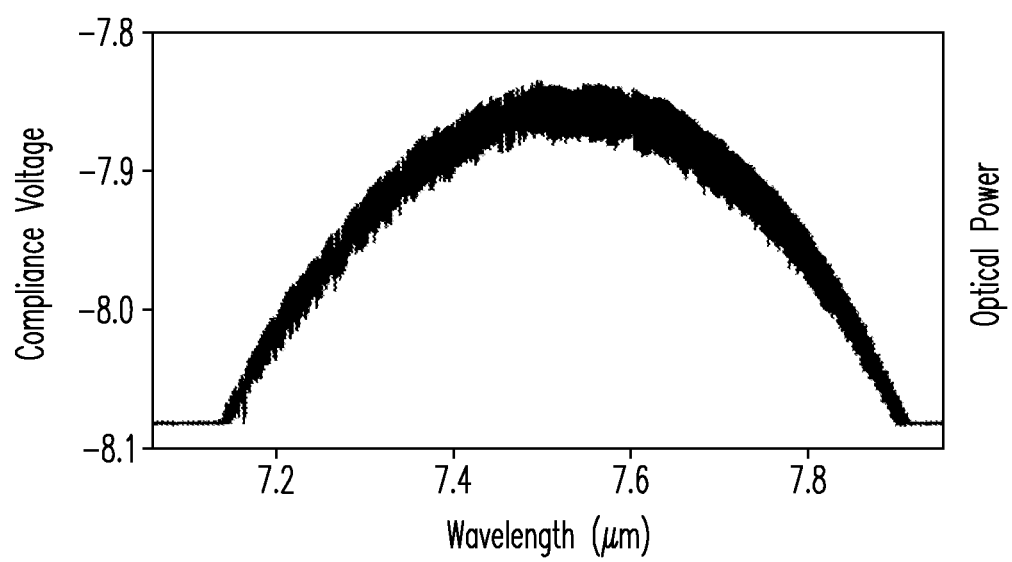
FIG. 8 shows a typical compliance voltage spectrum obtained from an external cavity laser as a function of wavelength.

FIG. 8 shows a typical compliance voltage spectrum obtained from an external cavity quantum cascade laser as a function of wavelength. Circulating power may be derived from this spectrum by applying a selected mathematical function as detailed herein.

Mathematical Functions

Mathematical functions include, but are not limited to, e.g., multiplication by constant value functions, multiplication functions, division functions, square-root functions, linear functions, polynomial functions, raising to a mathematical power functions, exponential functions, logarithmic functions, trigonometric functions, binomial functions, and combinations of these.

Laser Measurements

Laser measurements include, but are not limited to, e.g., absorption measurements, fluorescence measurements, reflection measurements, distance measurements, phase measurements, interferometric measurements, temperature measurements, density measurements, and combinations of these.

Laser Spectra

Laser spectra include, but are not limited to, e.g., absorption spectra, fluorescence spectra, reflection spectra, distance spectra, phase spectra, interferometric spectra, temperature spectra, density spectra, and combinations of these.

Sweeping of Laser

Sweeping of a laser as used herein may refer to continuous tuning of a laser wavelength, or may refer to a piece-wise tuning of a laser wavelength where the wavelength may be momentarily set to specific wavelength values for a selected time period or for selected time periods.

While exemplary embodiments of the present invention have been shown and described, it will be apparent to those skilled in the art that many changes and modifications may be made without departing from the invention in its true scope and broader aspects. The appended claims are therefore intended to cover all such changes and modifications as fall within the spirit and scope of the invention.

What is claimed is:

1. A method for obtaining a power-normalized laser measurement with an external cavity laser, comprising the steps of:
    driving a quantum cascade laser device disposed within the external cavity laser with a current through the quantum cascade laser device;
    obtaining a laser measurement with the external cavity laser;
    measuring a compliance voltage of the quantum cascade laser device; and
    combining the laser measurement with the compliance voltage to obtain a power-normalized laser measurement.

2. The method of claim 1, wherein obtaining the laser measurement is performed while measuring the compliance voltage.

3. The method of claim 1, wherein the combining includes combining the laser measurement with a value obtained from a mathematical function of the compliance voltage.

4. The method of claim 3, wherein the mathematical function is a single-valued function that includes the compliance voltage as the input and an optical power as the output.

5. The method of claim 3, wherein the mathematical function is a binary function that includes the compliance voltage and the current as the inputs and an optical power as the output.

6. The method of claim 1, further including sweeping a wavelength of the external cavity laser with a sweep signal while obtaining the laser measurement to generate a laser measurement spectrum as a function of the wavelength.

7. The method of claim 1, further including sweeping a wavelength of the external cavity laser with a sweep signal while measuring the compliance voltage to generate a compliance voltage spectrum as a function of the wavelength.

8. The method of claim 7, wherein the combining includes combining the laser measurement with a value obtained from a mathematical function of the compliance voltage.

9. The method of claim 8, wherein the mathematical function is a single-valued function that includes the compliance voltage spectrum as the input and an optical power spectrum as the output.

10. The method of claim 8, wherein the mathematical function is a binary function that includes the compliance voltage spectrum and the current as the inputs and an optical power spectrum as the output.

11. The method of claim 8, wherein the mathematical function is a binary function that includes the compliance voltage spectrum and the sweep signal as the inputs and an optical power spectrum as the output.

12. The method of claim 8, wherein the mathematical function is a ternary function that includes the compliance voltage spectrum, the current, and the sweep signal as the inputs and an optical power spectrum as the output.

* * * * *